United States Patent [19]

Ohi et al.

[11] Patent Number: 4,526,619

[45] Date of Patent: Jul. 2, 1985

[54] GYPSUM COMPOSITION FOR DENTURE INVESTMENT

[75] Inventors: Nobukazu Ohi, Fuchu; Koji Ohno, Akabanenishi; Satoshi Tosaki, Tokyo, all of Japan

[73] Assignee: G-C Dental Industrial Corp., Tokyo, Japan

[21] Appl. No.: 516,331

[22] Filed: Jul. 22, 1983

[30] Foreign Application Priority Data

Aug. 13, 1982 [JP] Japan ................................ 57-139799

[51] Int. Cl.$^3$ ............................................... C09K 3/00
[52] U.S. Cl. .................................... 106/35; 106/109; 433/199; 433/201
[58] Field of Search ................. 106/109, 35; 433/199, 433/201

[56] References Cited

U.S. PATENT DOCUMENTS 3,305,375  2/1967  Jakacki ................................ 106/109

*Primary Examiner*—Lorenzo B. Hayes
*Attorney, Agent, or Firm*—Oblon, Fisher, Spivak, McClelland & Maier

[57] ABSTRACT

A gypsum composition for denture investment consists of 100 parts by weight of a mixture of 50–90 parts by weight of α-Gypsum hemihydrate (α-CaSO$_4$.$\frac{1}{2}$H$_2$O) with 10–50 parts by weight of β-Gypsum hemihydrate (β-CaSO$_4$.$\frac{1}{2}$H$_2$O) and 0.2–2.0 parts by weight of a soluble potassium salt. As the soluble potassium salt, use may be made of one or more of potassium sulfate, potassium chloride and potassium tartrate. The gypsum composition may further include 0.5–5.0 parts by weight of dihydrate gypsum.

3 Claims, No Drawings 4,526,619

GYPSUM COMPOSITION FOR DENTURE INVESTMENT

BACKGROUND OF THE INVENTION

1. Field of the Invention

The present invention relates to a gypsum composition for denture investment used for the preparation of dental restorations such as complete or partial plate dentures with the use of resin providing a denture base material.

2. Description of the Prior Art

The dental profession has heretofore utilized as an important material a gypsum composition for denture investment serving as a mould material, when preparing dentures applied in the mouth. However, little proposal has been made of gypsum compositions for denture investment used as mould materials for holding artificial teeth. For that reason, use has generally been made of β-Gypsum hemihydrate ($\beta$-CaSO$_4$.$\frac{1}{2}$H$_2$O) exclusively used for building or ornamental purposes. However this β-Gypsum hemihydrate ($\beta$-CaSO$_4$.$\frac{1}{2}$H$_2$O) has a low wet-compressive strength 100 kgf/cm$^2$, that is considered to be the strength of the set gypsum per se. Therefore, when dough like resin is packed under pressure in a set mass covering artificial teeth, the thin gypsum portion surrounding the denture is readily damaged. In addition, due to the fact that the set gypsum shows a setting expansion of as high as 0.25%, the fitness of the plate having the denture invested therein drops upon the polymerization of resin and the artificial teeth shift to such an extent that restoration should be carried out for a very long period of time so as to reproduce the occlusal balance inherent in the patient. Futhermore, upon allowed to stand at room temperature, the setting time of β-Gypsum hemihydrate ($\beta$-CaSO$_4$.$\frac{1}{2}$H$_2$O) is delayed due to the absorption of moisture, thus posing problems in connection with storage stability.

To make up for the disadvantages of β-Gypsum hemihydrate ($\beta$-CaSO$_4$.$\frac{1}{2}$H$_2$O), in some cases, use may be made of α-Gypsum hemihydrate ($\alpha$-CaSO$_4$.$\frac{1}{2}$H$_2$O) that is dental model gypsum. Owing to the fact that the α-Gypsum hemihydrate ($\alpha$-CaSO$_4$.$\frac{1}{2}$H$_2$O) has originally been developed as a model material, it shows a wet-compressive strength on the order of 450 kgf/cm$^2$ upon set, that is quadruple as large as that of β-Gypsum hemihydrate ($\beta$-CaSO$_4$.$\frac{1}{2}$H$_2$O), with no substantial risk of being damaged. However, since there is little lowering of the compressive strength of the set gypsum upon the polymerization of denture base resin by heating, an extreme difficulty is encountered in removal of the denture after the resin has been polymerized by heating.

Clinical requirements strongly demanded for the gypsum compositions for denture investment are now that:

1. They should have a sufficient strength after setting, provided that at the time of removal of the denture upon the polymerization of resin by heating, they have a deteriorated strength to facilitate removal of the denture.

2. They should have a small setting expansion so that the dimensional accuracy of the denture is excellent upon the polymerization of resin by heating. And, 3. They should excel in storage stability.

SUMMARY OF THE INVENTION

In an effort to obtain a gypsum composition for denture investment which is free from the disadvantages as mentioned above and meets clinically high requirements, it has been found that a gypsum composition for denture investment meets the requirements currently demanded, consisting of a mixture of α-Gypsum hemihydrate ($\alpha$-CaSO$_4$.$\frac{1}{2}$H$_2$O) with β-Gypsum hemihydrate ($\beta$-CaSO$_4$.$\frac{1}{2}$H$_2$O) in a specific weight ratio, to which mixture of soluble potassium salt is added in a specific proportion. It has also been found that the said requirements are satisfied by a gypsum composition for denture investment consisting of the above-mentioned composition added with dihydrate gypsum in a specific proportion.

According to one aspect of the present invention, a gypsum composition for denture investment is provided, consisting of 100 parts by weight of a mixture of 50–90 parts by weight of α-Gypsum hemihydrate ($\alpha$-CaSO$_4$.$\frac{1}{2}$H$_2$O) with 10–50 parts by weight of β-Gypsum hemihydrate ($\beta$-CaSO$_4$.$\frac{1}{2}$H$_2$O), and 0.2–2.0 parts by weight of a soluble potassium salt.

According to another aspect of the present invention, a gypsum composition is provided, consisting of the gypsum composition obtained according to the said one aspect, to which 0.5–5.0 parts by weight of dihydrate gypsum is further added.

DETAILED EXPLANATION OF THE INVENTION

The upper and lower limits imposed upon the components or ingredients of the gypsum compositions of the present invention will now be explained in detail.

In the gypsum composition for denture investment, it is required that the set gypsum has a sufficient wet-compressive strength upon denture investment, and that the set gypsum has a deteriorated strength upon polymerization by heating. Thus, the first feature of the present invention consists in a specific combination of α-Gypsum hemihydrate ($\alpha$-CaSO$_4$.$\frac{1}{2}$H$_2$O) with β-Gypsum hemihydrate ($\beta$-CaSO$_4$.$\frac{1}{2}$H$_2$O). According to the present invention, 100 parts by weight of a gypsum mixture should consist of 50–90 parts by weight of α-Gypsum hemihydrate ($\alpha$-CaSO$_4$.$\frac{1}{2}$H$_2$O) and 10–50 parts by weight of β-Gypsum hemihydrate ($\beta$-CaSO$_4$.$\frac{1}{2}$H$_2$O). The α-Gypsum hemihydrate ($\alpha$-CaSO$_4$.$\frac{1}{2}$H$_2$O) is a component important for increasing the strength of the set gypsum and making the surface of the polymerized resin smooth. However, when the α-Gypsum hemihydrate amounts to 90 parts by weight or higher of 100 parts by weight of the gypsum mixture, the set gypsum has a sufficient wet compressive strength, but the set gypsum has too high a compressive strength upon heating, so that difficulty will be involved in removal of the denture. In an amount below 50 parts by weight, the set gypsum has a deteriorated compressive strength upon polymerization by heating, so that removal of the denture will be easy; however, the set gypsum has too low a wet-compressive strength, so that the thin set gypsum surrounding the denture will easily be damaged in packing of the denture base resin under pressure. Preferably, the α-Gypsum hemihydrate ($\alpha$-CaSO$_4$.$\frac{1}{2}$H$_2$O) should be used in an amount of 50–70 parts by weight, since the gypsum composition for denture investment should preferably have a wet-compressive strength of 150–240 kgf/cm$^2$ and a compressive strength upon heating of 80–110 kgf/cm$^2$. Use of the α-Gypsum hemihydrate ($\alpha$-CaSO$_4$.$\frac{1}{2}$H$_2$O) in an amount below 50 parts by weight is advantageous in that the compressive strength upon heating deteriorates, but is not preferable in view of manipulation in that the wet-compressive strength is too low. When the α-Gypsum hemihydrate (α-CaSO$_4$.$\frac{1}{2}$H$_2$O) exceeds 70 parts by weight, the wet-compressive strength is sufficient but the compressive strength upon heating becomes too high.

On the other hand, the β-Gypsum hemihydrate (β-CaSO$_4$.$\frac{1}{2}$H$_2$O) should be used in an amount of 10–50 parts by weight per 100 parts of the gypsum mixture for the following reasons. The β-Gypsum hemihydrate (β-CaSO$_4$.$\frac{1}{2}$H$_2$O) is a component for deteriorating the wet compressive strength of the set gypsum so as to facilitate removal of the denture. If the β-Gypsum hemihydrate (β-CaSO$_4$.$\frac{1}{2}$H$_2$O) is used an amount below 10 parts by weight per 100 parts by weight of the gypsum mixture, then the set gypsum will have a satisfactory strength (wet-compressive strength) but the set gypsum will have too high a compressive strength upon heating, thus rendering removal of the denture extremely difficult. Addition of the β-Gypsum hemihydrate (β-CaSO$_4$.$\frac{1}{2}$H$_2$O) in an amount exceeding 50 parts by weight causes that the set gypsum has a deteriorated strength upon polymerization by heating, so that removal of the denture will be facilitated. However, the strength (wet-compressive strength) of the set gypsum is so deteriorated that the thin set gypsum surrounding the denture will easily be damaged in packing of the denture base resin under pressure. Most preferably, the β-Gypsum hemihydrate (β-CaSO$_4$.$\frac{1}{2}$H$_2$O) should be used in an amount of 30–50 parts by weight per 100 parts by weight of the gypsum mixture, since, as discussed above, the gypsum composition for denture investment should have a wet compressive strength of 150–240 kgf/cm$^2$ and a compressive strength upon heating of 80–110 kgf/cm$^2$. If the β-Gypsum hemihydrate (β-CaSO$_4$.$\frac{1}{2}$H$_2$O) is used in an amount below 30 parts by weight per 100 parts by weight of the gypsum mixture, then the wet-compressive strength will be satisfactory but the compressive strength upon heating will become too low. In an amount exceeding 50 parts by weight, the compressive strength upon heating deteriorates, but the wet compressive strength becomes too low.

A second feature of the present invention consists in the use of a soluble potassium salt which is added to a mixture of 50–90 parts by weight of α-Gypsum hemihydrate (α-CaSO$_4$.$\frac{1}{2}$H$_2$O) with 10–50 parts by weight of β-Gypsum hemihydrate (β-CaSO$_4$.$\frac{1}{2}$H$_2$O) in a specific proportion. The soluble potassium salt is a component for reducing the setting expansion of the set gypsum, thereby to improve the dimensional accuracy of the denture after polymerization of the denture base resin by heating. For that purpose, use may be made of one or more of potassium sulfate, potassium chloride, potassium tartrate and the like. The soluble potassium salt(s) should be added per 100 parts by weight of the gypsum mixture in an amount of 0.2–2.0 parts by weight. In an amount below 0.2 parts by weight, the potassium salt has no effect upon reductions in the setting expansion of the set gypsum. Addition of the potassium salt in an amount exceeding 2.0 parts by weight is unpreferable since the setting time of the gypsum is too short with the result that both workability and storage stability drop.

Combination of the soluble potassium salt, for instance, potassium sulfate and potassium chloride, potassium sulfate and potassium tartrate, and potassium chloride and potassium tartrate should preferably be applied, since their amount is reduced as compared with the addition of one soluble potassium salt, yet it is possible to suppress the setting expansion of the gypsum. In addition, the setting time of the gypsum is so moderate that improved workability and storage stability are obtained. To reduce the setting expansion of the gypsum composition for denture investment to below 0.12%, the soluble potassium salt should most preferably be used in an amount of no less than 0.5 parts by weight, since a setting expansion of not more than 0.12% is further desirable for improving the dimensional accuracy of the resin plate denture after polymerization by heating. Furthermore, it is preferable to use the soluble potassium salt in an amount of no greater than 1.8 parts by weight, since neither premature setting of the gypsum nor lowering of storage stability takes place.

In view of the currently demanded requirements, the gypsum composition for denture investment consisting of 100 parts by weight of a mixture of α-Gypsum hemihydrate (α-CaSO$_4$.$\frac{1}{2}$H$_2$O) with β-Gypsum hemihydrate (β-CaSO$_4$.$\frac{1}{2}$H$_2$O) and 0.2–2.0 parts by weight of a soluble potassium salt(s) may function well. However, it has been found that further preferable results are obtained if 0.5–5.0 parts by weight of dihydrate gypsum are added to 100 parts by weight of a mixture of α-Gypsum hemihydrate (α-CaSO$_4$.$\frac{1}{2}$H$_2$O) with β-Gypsum hemihydrate (β-CaSO$_4$.$\frac{1}{2}$H$_2$O). The dihydrate gypsum is a component for improving the storage stability of the gypsum composition for denture investment, which shall be estimated in terms of a delay in setting time that is calculated by subtracting the initial setting time from the setting time after the lapse of predetermined days. Use of the dihydrate gypsum in an amount exceeding 5.0 parts by weight per 100 parts by weight by the gypsum mixture is rather unpreferable, since the storage stability of the gypsum composition for denture investment deteriorates, and the setting time is too shortened to give rise to problems in connection with workability. The dihydrate gypsum in an amount below 0.5 parts byweight shows less effect upon improvement in the storage stability of the gypsum composition for denture investment.

In general, the dihydrate gypsum contains free water. It is thus noted that dihydrate gypsum containing more than 0.7% by weight of free water may deteriorate the storage stability of the gypsum composition for denture investment. In view of the fact that further preferable requirements for the gypsum composition for denture investment are that the storage stability is defined in terms of a delay within two minutes after 60 days, the dihydrate gypsum should be added in an amount of 0.5 to 4.5 parts by weight. This is because in an amount below 0.5 parts by weight there is a delay of three minutes after 60 days, and an amount of no more than 4.5 parts by weight there is an ample period for setting of the gypsum composition for denture investment in view of workability.

The present invention will now be explained with reference to examples and comparative examples. In the examples and comparative examples (except No. 11), α-Gypsum hemihydrate (α-CaSO$_4$.$\frac{1}{2}$H$_2$O) powders were milled together in a ball mill while mixed, or not mixed, with one or more of potassium sulfate, potassium chloride and potassium tartrate that were soluble potassium salts and/or dihydrate gypsum, and passed through a 100 mesh sieve to obtain fine powders. The thus obtained fine powders were mixed, or not mixed, with β-Gypsum hemihydrate (β-CaSO$_4$.$\frac{1}{2}$H$_2$O), and passed through a 100-mesh sieve to obtain fine powders. In this manner, the gypsum compositions for denture investment were prepared. In Comparative Example 11, β-Gypsum hemihydrate (β-CaSO$_4$.½H$_2$O) passed through a 100-mesh sieve was used. The amount of water used was determined according to the testing method JIS T6605 (Dental Stone).

With the aid of a rubber ball and a plaster spatula usually employed for gypsum mixing in dentistry, 100 grams of samples were mixed to water together for 60 seconds at a rate of 100 r.p.m. After metering with a glass tube 20 mm in diameter, 10 ml of samples were slowly extruded onto a glass plate. After two minutes, a glass plate and a weight, weighing 120 grams in all, were placed on the samples for their extension. The maximum and minimum diameters between the samples extended in parallel were measured. When the average value reached 39-41 mm, the amount of water was taken to be an amount of water for standard consistency. These tests were carried at room temperature ranging 15° to 20° C. Setting time was measured by filling the samples mixed to the standard consistency in a cylindrical metal model 20 mm in inner diameter and 30 mm in height and measuring a time period from the charging of the samples in water to 1 mm immersion of a Vicat needle weighing 300 grams and 2 mm in diameter. Wet-compressive strength testing was carried out by charging the samples mixed to the standard consistency in a cylindrical metal model 20 mm in inner diameter and 30 mm in height, removing them out of the model after setting, allowing them to stand at room temperature, and determining the compressive strength thereof at a loading rate of 1 mm/min. with the aid of a compressive tester three hours after the charging of the samples in water. Compressive-strength-upon-heating-testing was effected by charging in water the samples prepared in the same manner as in wet-compressive strength testing. Three hours after the charging of the samples in water, the samples were maintained in hot water of 90°-95° C. for one hour, and cooled in water of room temperature for 10 minutes to determine the compressive strength thereof at a loading rate of 1 mm/min. with the aid of a compressive strength tester. Storage stability testing was undertaken by storing the powdery gypsum compositions for denture investment, which had been charged in a polyethylene bag, in a thermohygrostat maintained at a temperature of 37° and a humidity of 100% and determining a delay in setting by the aforesaid setting time-measuring method. Setting expansion testing was carried out by determining the setting expansion of the samples having the standard water content two hours after the charging thereof in water with the use of a tester comprising a rectangular metal model 10 cm in length, 3 cm in width and 3 cm in height and including an expansion-measuring dial gauge bearing 0.01 mm readings.

The results are given in the following table.

| Nos | | Composition Component | Part by Weight | Standard Water Content (wt %) | Initial Setting Time in Minute | Compressive Strength (kgf/cm$^2$) Wet | Heating | Storage Stability after 60 days (min.) | Setting Expansion (%) |
|---|---|---|---|---|---|---|---|---|---|
| 1 | Example | α-Gypsum hemihydrate(α-CaSO$_4$.½H$_2$O) | 90 | 0.44 | 7 | 289 | 206 | 9 | 0.15 |
| | | β-Gypsum hemihydrate(β-CaSO$_4$.½H$_2$O) | 10 | | | | | | |
| | | Dihydrate gypsum | 1 | | | | | | |
| | | Potassium sulfate | 0.5 | | | | | | |
| 2 | Example | α-Gypsum hemihydrate(α-CaSO$_4$.½H$_2$O) | 80 | 0.42 | 8 | 267 | 196 | 10 | 0.14 |
| | | β-Gypsum hemihydrate(β-CaSO$_4$.½H$_2$O) | 20 | | | | | | |
| | | Dihydrate gypsum | 2 | | | | | | |
| | | Potassium chloride | 0.2 | | | | | | |
| | | Potassium sulfate | 0.2 | | | | | | |
| 3 | Example | α-Gypsum hemihydrate(α-CaSO$_4$.½H$_2$O) | 70 | 0.40 | 8 | 235 | 173 | 10 | 0.10 |
| | | β-Gypsum hemihydrate(β-CaSO$_4$.½H$_2$O) | 30 | | | | | | |
| | | Dihydrate gypsum | 3 | | | | | | |
| | | Potassium tartrate | 0.6 | | | | | | |
| 4 | Example | α-Gypsum hemihydrate(α-CaSO$_4$.½H$_2$O) | 60 | 0.38 | 9 | 183 | 108 | 10 | 0.08 |
| | | β-Gypsum hemihydrate(β-CaSO$_4$.½H$_2$O) | 40 | | | | | | |
| | | Dihydrate gypsum | 4 | | | | | | |
| | | Potassium sulfate | 0.9 | | | | | | |
| 5 | Example | α-Gypsum hemihydrate(α-CaSO$_4$.½H$_2$O) | 50 | 0.38 | 8 | 170 | 72 | 10 | 0.09 |
| | | β-Gypsum hemihydrate(β-CaSO$_4$.½H$_2$O) | 50 | | | | | | |
| | | Dihydrate gypsum | 4.5 | | | | | | |
| | | Potassium sulfate | 0.8 | | | | | | |
| | | Potassium tartrate | 1.0 | | | | | | |
| 6 | Example | α-Gypsum hemihydrate(α-CaSO$_4$.½H$_2$O) | 60 | 0.38 | 9 | 187 | 109 | 17 | 0.10 |
| | | β-Gypsum hemihydrate(β-CaSO$_4$.½H$_2$O) | 40 | | | | | | |
| | | Potassium sulfate | 0.8 | | | | | | |
| 7 | Example | α-Gypsum hemihydrate(α-CaSO$_4$.½H$_2$O) | 60 | 0.38 | 10 | 184 | 106 | 12 | 0.06 |
| | | β-Gypsum hemihydrate(β-CaSO$_4$.½H$_2$O) | 20 | | | | | | |
| | | Dihydrate gypsum | 0.5 | | | | | | |
| | | Potassium sulfate | 2 | | | | | | |
| 8 | Example | α-Gypsum hemihydrate(α-CaSO$_4$.½H$_2$O) | 60 | 0.38 | 3 | 180 | 110 | 12 | 0.06 |
| | | β-Gypsum hemihydrate(β-CaSO$_4$.½H$_2$O) | 40 | | | | | | |
| | | Potassium sulfate | 2 | | | | | | |
| 9 | Comparative Example | α-Gypsum hemihydrate(α-CaSO$_4$.½H$_2$O) | 40 | 0.40 | 5 | 125 | 68 | 13 | 0.17 |
| | | β-Gypsum hemihydrate(β-CaSO$_4$.½H$_2$O) | 50 | | | | | | |
| | | Dihydrate gypsum | 7 | | | | | | |
| | | Potassium tartrate | 0.8 | | | | | | |
| 10 | Comparative Example | α-Gypsum hemihydrate(α-CaSO$_4$.½H$_2$O) | 60 | 0.38 | 8 | 195 | 145 | 14 | 0.40 |
| | | β-Gypsum hemihydrate(β-CaSO$_4$.½H$_2$O) | 40 | | | | | | |
| | | Dihydrate gypsum | 3 | | | | | | |
| 11 | Comparative Example | β-Gypsum hemihydrate(β-CaSO$_4$.½H$_2$O) | | 0.60 | 12 | 100 | 84 | 24 | 0.25 |
| 12 | Comparative | α-Gypsum hemihydrate(α-CaSO$_4$.½H$_2$O) | | 0.28 | 10 | 450 | 408 | 17 | 0.40 |

| Nos | Composition Component | Part by Weight | Standard Water Content (wt %) | Initial Setting Time in Minute | Compressive Strength (kgf/cm²) Wet | Compressive Strength (kgf/cm²) Heating | Storage Stability after 60 days (min.) | Setting Expansion (%) |
|---|---|---|---|---|---|---|---|---|
| Example | | | | | | | | |

As will be appreciated from the table, the composition consisting only of β-Gypsum hemihydrate (β-CaSO$_4$.$\frac{1}{2}$H$_2$O) (Comparative Example 11) has a wet compressive strength of as low as 100 kgf/cm², and the composition having a larger dihydrate gypsum content (Comparative Example 9) has a low wet-compressive strength on the order of 125 kgf/cm², which mean that these compositions have their strength properties unsuitable for use in the gypsum compositions for denture investment. The composition consisting of only α-Gypsum hemihydrate (α-CaSO$_4$.$\frac{1}{2}$H$_2$O) (Comparative Example 12) has a wet-compressive strength of as high as 450 kgf/cm², and the composition free from any soluble potassium salt (Comparative Examples 10 and 12) has a setting expansion of as large as 0.40%. These compositions are all found to be unsuitable for use in the gypsum compositions for denture investment.

Values obtained by subtracting the compressive strength upon heating from the wet-compressive strength are 50, 16 and 42 kgf/cm² in Comparative Example 10, 11 and 12, respectively, while those values are 83, 71, 62, 75, 98, 78, 78 and 70 kgf/cm² in Examples 1 to 8 inclusive according to the present invention. Thus, the examples according to the present invention are larger than the comparative examples with respect to those values. In addition, the gypsum compositions for denture investment according to the present invention have a sufficient wet-compressive strength corresponding to the strength of the set mass, and show a satisfactorily deteriorated strength upon polymerization by heating, thus posing no problems in connection with workability. With respect to storage stability, differences between the setting time after 60 days and the initial setting time are 8, 6, 12 and 7 minutes in Comparative Examples 9-12, respectively, while they are 8 and 9 minutes in Examples 6 and 8 wherein any dihydrate gypsum was not used at all. On the other hand, in Examples 1 to 5 and 7 wherein dihydrate gypsum was in specific proportions, a delay within 2 minutes is found. This means that no problem arises in connection with storage stability.

The gypsum compositions for denture investment according to the present invention show a low setting expansion on the order of no more than 0.15%, and found to improve the accuracy of the denture to be prepared. However, the compositions according to the comparative examples are so increased in setting expansion that it is impossible to prepare dentures accurately.

As mentioned above, the gypsum composition for denture investment according to the present invention meets a variety of requirements imposed upon the preparation of dentures. Thus, the present invention presents a breakthrough in dentistry.

What is claimed is:

1. A gypsum composition for denture investment consisting of 100 parts by weight of a mixture of 50-90 parts by weight of α-Gypsum hemihydrate (α-CaSO$_4$.$\frac{1}{2}$H$_2$O), 10-50 parts by weight of β-Gypsum hemihydrate (β-CaSO$_4$.$\frac{1}{2}$H$_2$O), 0.2-2.0 parts by weight of a soluble potassium salt, and 0.5-5.0 parts by weight of gypsum dihydrate.

2. A gypsum composition as recited in claim 1, wherein the potassium salt is selected from the group consisting of potassium sulfate, potassium chloride, potassium tartrate and mixtures thereof.

3. A gypsum composition as recited in claim 1 or 2, in which the gypsum dihydrate contains up to 0.7% by weight of free water.

* * * * *